(12) United States Patent
Uehara

(10) Patent No.: US 6,485,421 B2
(45) Date of Patent: Nov. 26, 2002

(54) ULTRASONIC IMAGING SYSTEM AND DISPLAY DEVICE

(75) Inventor: Shoichi Uehara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/928,180

(22) Filed: Aug. 10, 2001

(65) Prior Publication Data

US 2002/0028996 A1 Mar. 7, 2002

(30) Foreign Application Priority Data

Sep. 7, 2000 (JP) .................................. 2000-271120
Nov. 8, 2000 (JP) .................................. 2000-339778

(51) Int. Cl.$^7$ ................................................ A61B 8/00
(52) U.S. Cl. ........................................................ 600/437
(58) Field of Search ................................ 600/437, 443, 600/447; 73/625–626; 345/63, 77, 102, 107, 204, 207, 211, 214

(56) References Cited

U.S. PATENT DOCUMENTS

| | | | | |
|---|---|---|---|---|
| 4,760,389 A | * | 7/1988 | Aoki et al. | 340/719 |
| 5,315,695 A | * | 5/1994 | Saito et al. | 395/132 |
| 5,406,305 A | * | 4/1995 | Shimomura et al. | 345/102 |
| 5,690,114 A | * | 11/1997 | Chiang et al. | 600/447 |
| 5,760,760 A | * | 6/1998 | Helms | 345/102 |
| 5,817,024 A | * | 10/1998 | Ogle et al. | 600/447 |
| 6,094,185 A | * | 7/2000 | Shirriff | 345/102 |

FOREIGN PATENT DOCUMENTS

| | | |
|---|---|---|
| EP | 0833266 | 4/1998 |
| WO | 9926224 | 5/1999 |

* cited by examiner

Primary Examiner—Francis J. Jaworski
(74) Attorney, Agent, or Firm—Moonray Kojima

(57) ABSTRACT

To make it possible to lower the luminance of an LCD to a level suitable for a dark place, either first image data based on which a predetermined image is displayed or second image data based on which the same image is displayed with lower luminance than the predetermined image based on the first image data is transferred to an LCD via a selecting means.

9 Claims, 15 Drawing Sheets

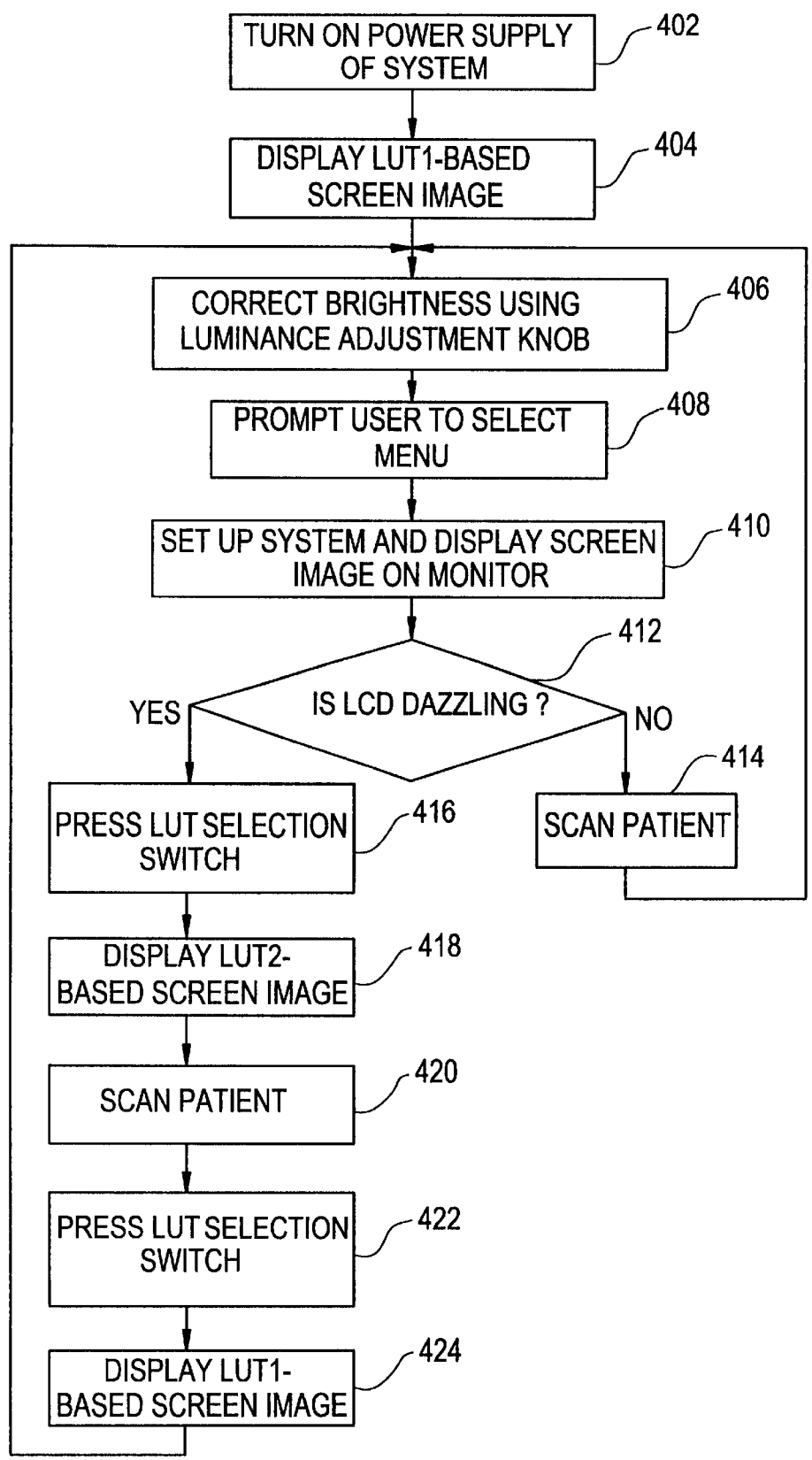

BRIGHT SCREEN

DARK SCREEN

DARKER SCREEN

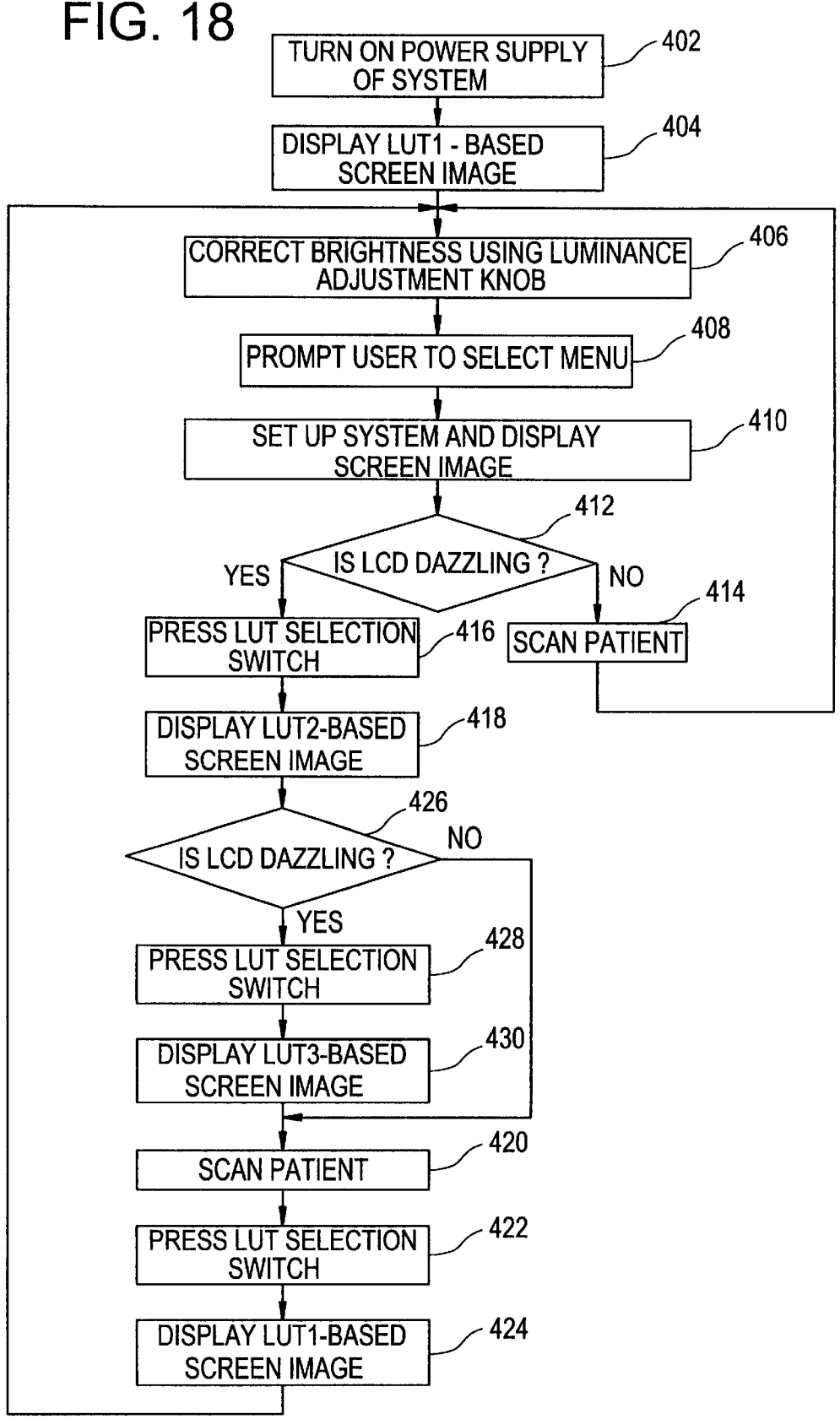

ULTRASONIC IMAGING SYSTEM AND DISPLAY DEVICE

BACKGROUND OF THE INVENTION

The present invention relates to an ultrasonic imaging system and a display device. More particularly, the present invention is concerned with an ultrasonic imaging system including a main display device that displays ultrasonic images and an auxiliary display device that displays information that helps a user operate the ultrasonic imaging system, and a display device to be used in combination with the ultrasonic imaging system.

RELATED ART

For ultrasonic imaging, echoes of ultrasonic waves transmitted to the interior of an object are used to produce tomographic images that are displayed as B-mode images. Moreover, Doppler shifts occurring in the echoes of the ultrasonic waves are utilized to produce dynamic images of a blood flow or the like that are displayed as color Doppler images.

An ultrasonic imaging system includes an operator console, with which a user can freely operate the ultrasonic imaging system. The operator control includes a graphic display so as to cope with diverse requirements for the operation.

The operator console including the graphic display switches screens so as to change the features of the operator console. Operation is performed with utilization of graphical user interfaces implemented in the screens.

A liquid crystal display is adopted as the graphic display. A transmissive LCD that radiates light, which is emitted from behind, forwards through a liquid crystal matrix so as to display images is adopted from among various types of LCDs.

The transmissive LCD exhibits high luminance so as to offer excellent visibility even in a bright room or the like. The screen of the LCD tends to be too bright for ultrasonic imaging systems that are often used in dark environments.

Therefore, for example, when images being produced are displayed on a cathode-ray tube (CRT) display for observation, the screen of the LCD that is much brighter than the display screen of the CRT dazzles a user.

The luminance of the LCD can be somewhat lowered by adjusting illumination light emitted from behind. However, there is a limit in reduction of illumination light due to the properties of a light source, and even if the amount of illumination light is decreased to the lowest limit, the LCD may still be too bright

SUMMARY OF THE INVENTION

An object of the present invention is to realize an ultrasonic imaging system in which the luminance of an LCD in an operator console can be lowered to a level suitable for a dark place, and a display device in which the luminance of an LCD can be lowered to a level suitable for a dark place.

(1) According to one aspect of the present invention for accomplishing the foregoing object, there is provided an ultrasonic imaging system including imaging means for transmitting ultrasonic waves and producing images according to the received echoes of the ultrasonic waves; main display means for displaying the images; and auxiliary display means for displaying information that helps a user operate the imaging system, wherein the auxiliary display means includes an LCD for radiating light, which is emitted from behind, forwards through a liquid crystal matrix whose transmittance can be controlled at each pixel location, and thus displaying images; first memory means in which first image data based on which a predetermined image is displayed on the LCD is stored, second memory means in which second image data based on which the same image as the predetermined image is displayed on the LCD with lower luminance than the predetermined image based on the first image data is stored; and image data providing means for providing the LCD with either the first image data or the second image data that is selected.

(2) According to another aspect of the present invention for accomplishing the foregoing object, there is provided a display device including an LCD for radiating light, which is emitted from behind, forwards through a liquid crystal matrix whose transmittance can be controlled at each pixel location, and thus displaying images; first memory means in which first image data based on which a predetermined image is displayed on the LCD is stored; second memory means in which second image data based on which the same image as the predetermined image is displayed on the LCD with lower luminance than the predetermined image based on the first image data is stored; and image data providing means for providing the LCD with either the first image data or the second image data that is selected.

According to the aspects (1) and (2) of the present invention, the LCD is selectively provided with either of the first image data based on which the predetermined image is displayed, or the second image data based on which the same image is displayed with lower luminance than the predetermined image based on the first image data. The luminance of the LCD on which the same image is displayed can be changed between two levels.

(3) According to another aspect of the present invention for accomplishing the aforesaid object, there is provided an ultrasonic imaging system including imaging means for transmitting ultrasonic waves and producing images according to the received echoes of the ultrasonic waves; main display means for displaying the images; and auxiliary display means for displaying information that helps a user operate the imaging system, wherein the auxiliary display means includes an LCD for radiating light, which is emitted from behind, forwards through a liquid crystal matrix that permits control of the hue of each pixel, and thus displaying images; first memory means in which first image data based on which a predetermined image is displayed on the LCD is stored; second memory means in which second image data based on which the same image as the predetermined image is displayed on the LCD at darker hue than the predetermined image based on the first image data is stored; and image data providing means for providing the LCD with either the first image data or the second image data that is selected.

(4) According to another aspect of the present invention for accomplishing the aforesaid object, there is provided a display device including an LCD for radiating light, which is emitted from behind, forwards through a liquid crystal matrix that permits control of the hue of each pixel, and thus displaying images; first memory means in which first image data based on which a predetermined image is displayed on the LCD is stored; second memory means in which second image data based on which the same image as the predetermined image is displayed on the LCD at darker hue than the predetermined image based on the first image data is stored; and image data providing means for providing the LCD with either the first image data or the second image data that is selected.

According to the aspects (3) and (4) of the present invention, the LCD is selectively provided with either the first image data based on which the predetermined image is displayed, or the second image data based on which the same image is displayed at darker hue than the predetermined image based on the first image data. Consequently, the brightness of the same image to be displayed can be changed between two levels.

(5) According to another aspect of the present invention for accomplishing the aforesaid object, there is provided an ultrasonic imaging system including imaging means for transmitting ultrasonic waves and producing images according to the received echoes of the ultrasonic waves; main display means for displaying the images; and auxiliary display means for displaying information that helps a user operate the imaging system, wherein the auxiliary display means includes an LCD for radiating light, which is emitted from behind, forwards through a liquid crystal matrix that permits control of the hue of each pixel, and thus displaying images; first memory means in which first image data based on which a predetermined image is displayed on the LCD is stored; second memory means in which second image data based on which the same image as the predetermined image is displayed on the LCD at darker hue than the predetermined image based on the first image data is stored; third memory means in which third image data based on which the same image as the predetermined image is displayed on the LCD in a darker achromatic color than the image based on the second image data is stored; and image data providing means for providing the LCD with any of the first image data, the second image data, and the third image data which is selected.

(6) According to another aspect of the present invention for accomplishing the aforesaid object, there is provided a display device including an LCD for radiating light, which is emitted from behind, forwards through a liquid crystal matrix that permits control of the hue of each pixel, and thus displaying images; first memory means in which first image data based on which a predetermined image is displayed on the LCD is stored; second memory means in which second image data based on which the same image as the predetermined image is displayed on the LCD at darker hue than the predetermined image based on the first image data is stored; third memory means in which third image data based on which the same image as the predetermined image is displayed on the LCD in a darker achromatic color than the image based on the second image data is stored; and image data providing means for providing the LCD with any of the first image data, the second image data, and the third image data which is selected.

According to the aspects (5) and (6) of the present invention, the LCD is selectively provided with any of the first image data based on which the predetermined image is displayed, second image data based on which the as the image as the predetermined image is displayed at darker hue than the predetermined image based on the first image data, and third image data based on which the same image as the predetermined image is displayed in a darker achromatic color than the image based on the second image data. The luminance of the LCD on which the same image is displayed can be changed among three levels.

(7) According to another aspect of the present invention for accomplishing the aforesaid object, there is provided an ultrasonic imaging system including imaging means for transmitting ultrasonic waves and producing images according to the received echoes of the ultrasonic waves; main display means for displaying the images; and auxiliary display means, wherein the auxiliary display means includes an LCD for radiating light, which is emitted from behind, forwards through a liquid crystal matrix that permits control of the lightness and hue of each pixel, and thus displaying images; fist memory means in which first image data based on which a predetermined image is displayed on the LCD is stored; second memory means in which second image data based on which the same image as the predetermined image is displayed on the LCD at lower lightness and darker hue than the predetermined image based on the first image data is stored; and image data providing means for providing the LCD with either the first image data or the second image data that is selected.

(8) According to another aspect of the present invention for accomplishing the aforesaid object, there is provided a display device including an LCD for radiating light, which is emitted from behind, forwards through a liquid crystal matrix that permits control of the lightness and hue of each pixel, and thus displaying images; first memory means in which first image data based on which a predetermined image is displayed on the LCD is stored; second memory means in which second image data based on which the same image as the predetermined image is displayed on the LCD at lower lightness and darker hue than the predetermined image based on the first image data is stored; and image data providing means for providing the LCD with either the first image data or the second image data that is selected.

According to the aspects (7) and (8) of the present invention, the LCD is selectively provided with either the first image data based on which the predetermined image is displayed, or the second image data based on which the same image is displayed at lower lightness and darker hue than the predetermined image based on the first image data. Consequently, the luminance of the LCD on which the same image is displayed can be changed between two levels.

(9) According to another aspect of the present invention for accomplishing the aforesaid object, there is provided an ultrasonic imaging system consisting of imaging means for transmitting ultrasonic waves and producing images according to the received echoes of the ultrasonic waves; main display means for displaying the images; and auxiliary display means, wherein the auxiliary display means includes an LCD for radiating light, which is emitted from behind, forwards through a liquid crystal matrix that permits control of the lightness and hue of each pixel, and thus displaying images; fi memory means in which first image data based on which a predetermined image is displayed on the LCD is stored; second memory means in which second image data based on which the same image as the predetermined image is displayed on the LCD at lower lightness and darker hue than the predetermined image based on the first image data is stored; third memory means in which third image data based on which the same image as the predetermined image is displayed on the LCD in a darker achromatic color than the image based on the second image data is stored; and image data providing means for providing the LCD with any of the first image data, the second image data, and the third image data which is selected.

(10) According to another aspect of the present invention for accomplishing the aforesaid object, there is provided a display device consisting mainly of an LCD for radiating light, which is emitted from behind, forwards through a liquid crystal matrix that permits control of the lightness and hue of each pixel, and thus displaying images; first memory means in which first image data based on which a predetermined image is displayed on the LCD is stored; second memory means in which second image data based on which the same image as the predetermined image is displayed on the LCD at lower lightness and darker hue than the predetermined image based on the first image data is stored; third memory means in which third image data based on which the same image as the predetermined image is displayed on the LCD in a darker achromatic color than the image based on the second image data is stored; and image data providing means for providing the LCD with any of the first image data, the second image data, and the third image data which is selected.

According to the aspects (9) and (10) of the present invention, the LCD is selectively provided with any of the first image data based on which the predetermined image is displayed, second image data based on which the same image as the predetermined image is displayed at lower lightness and darker hue than the predetermined image based on the first image data, and third image data based on which the same image is displayed in a darker achromatic color than the image based on the second image data. Consequently, the luminance of the LCD on which the same image is displayed can be changed among three levels.

According to the foregoing aspects of the present invention, preferably, a user selects image data to be provided for the LCD, and thus changes the luminance of the display screen of the LCD according to the user's intention.

According to the foregoing aspects of the present invention, preferably, an amount of light to be emitted to the LCD from behind is varied in order to thus adjust an amount of illumination light and eventually control the luminance of the display screen of the LCD.

As described above, according to the present invention, an ultrasonic imaging system capable of lower the luminance of an LCD included in an operator console to a level suitable for a dark place is realized. Also realized is a display device capable of lowing the luminance of an LCD thereof to a level suitable for a dark place.

Further objects and advantages of the present invention will be apparent from the following description of the preferred embodiments of the invention as illustrated in the accompanying drawings.

BRIEF DESCRIPTION OF THE DRAWINGS

FIG. 15 is a flowchart describing actions to be performed by the system in accordance with the embodiment of the present invention.

FIG. 18 is a flowchart describing actions to be performed by the system in accordance with the embodiment of the present invention.

DETAILED DESCRIPTION OF THE INVENTION

Figure 1:
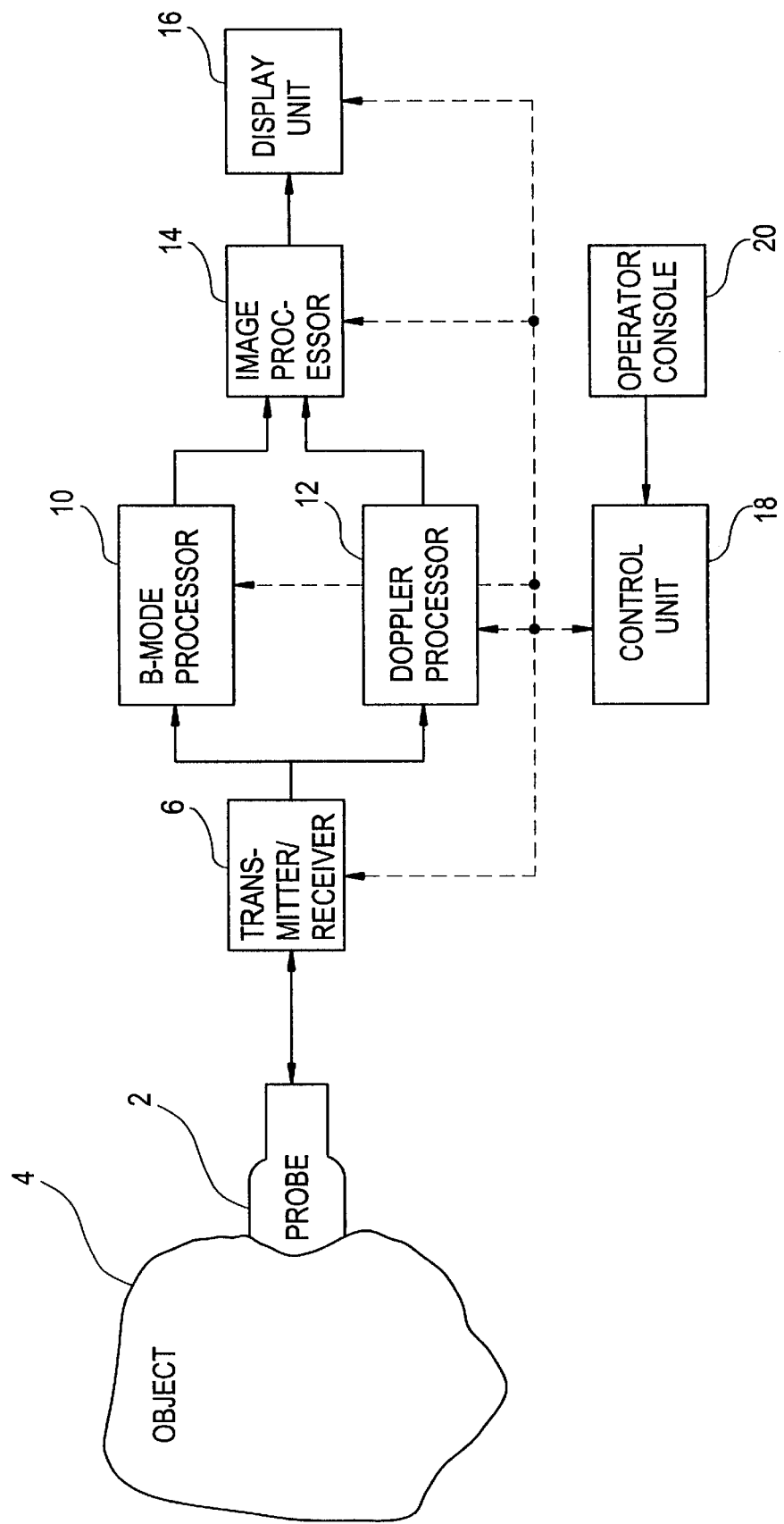
FIG. 1 is a block diagram of a system according to an embodiment of the present invention.

An embodiment of the present invention will be described with reference to the drawings below. Incidentally, the present invention will not be limited to the embodiment. FIG. 1 is a block diagram showing an ultrasonic imaging system. The system is an embodiment of the present invention. The configuration of the system provides an embodiment of an ultrasonic imaging system in accordance wit the present invention.

As shown in FIG. 1, the ultrasonic imaging system includes an ultrasonic probe 2. The ultrasonic probe includes an array of a plurality of ultrasonic transducers not shown. Each ultrasonic transducer is made of a piezoelectric material such as ceramics of lead zirconate (Zr) titanate (Ti) (PZT). A user brings the ultrasonic probe 2 into contact with an object 4.

The ultrasonic probe 2 is connected to a transmitter-receiver 6. The transmitter-receiver 6 applies a driving signal to the ultrasonic probe 2 and thus causes the ultrasonic probe 2 to transmit ultrasonic waves. The transmitter-receiver 6 receives echoes via the ultrasonic probe 2.

Figure 2:
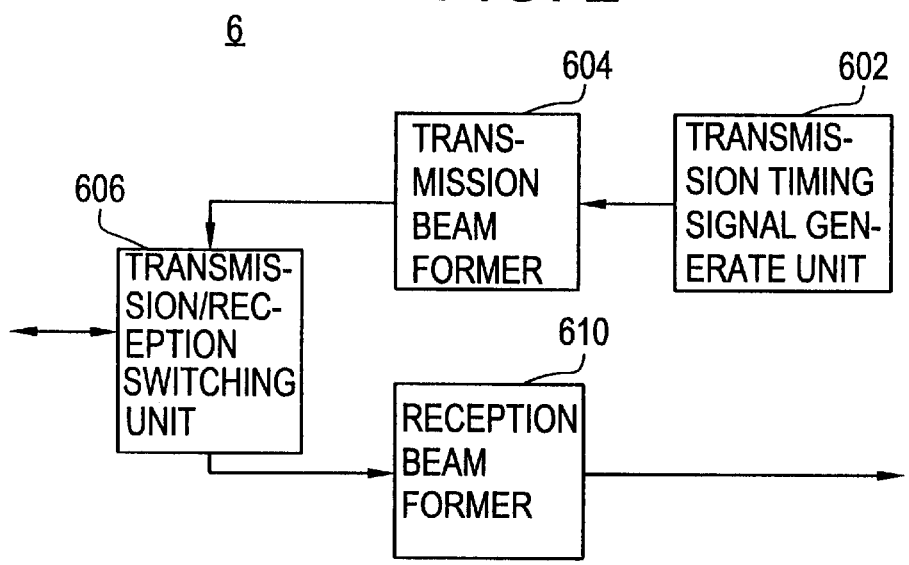
FIG. 2 is a block diagram of a transmitter-receiver employed in the system shown in FIG. 1.

FIG. 2 is a block diagram showing the transmitter-receiver 6. As illustrated, the transmitter-receiver 6 includes a transmission timing signal generation unit 602. The transmission timing signal generation unit 602 cyclically generates a transmission timing signal and transfers it to a transmission beam former 604. The cycle of the transmission timing signal is controlled by a control unit 18 that will be described later.

The transmission beam former 604 forms a beam to be transmitted, that is, generates a beam forming signal, with which a beam is shaped from ultrasonic waves oriented in a predetermined direction, according to the transmission timing signal. The beam forming signal consists of a plurality of driving signals that have a time difference associated with the direction. Beam forming is controlled by the control unit 18 that will be described later. The transmission beam former 604 transfers the transmission beam forming signal to a transmission/reception switching unit 606.

The transmission/reception switching unit 606 transfers the beam forming signal to the array of ultrasonic transducers. In the ultrasonic transducer array, the plurality of ultrasonic transducers that form a transmission aperture generates ultrasonic waves that have a phase difference associated with the time difference among the driving signals. The wave fronts of the ultrasonic waves are synthesized to form an ultrasonic beam that is propagated along an acoustic line oriented in the predetermined direction.

A reception beam former 610 is connected to the transmission/reception switching unit 606. The transmission/reception switching unit 606 transfers the plurality of echoes received by a reception aperture formed by part of the ultrasonic transducer array into the reception beam former 610. The reception beam former 610 forms a beam to be received, that is, produces an ultrasonic beam to be propagated along the acoustic line, causes the plurality of received echoes to have a time difference so as to adjust the phases of the echoes, and sums up the resultant echoes to produce an echo signal that is transmitted over the acoustic line oriented in the predetermined direction. The beam forming of a beam to be received is controlled by the control unit 18 to be described later.

Figure 3:
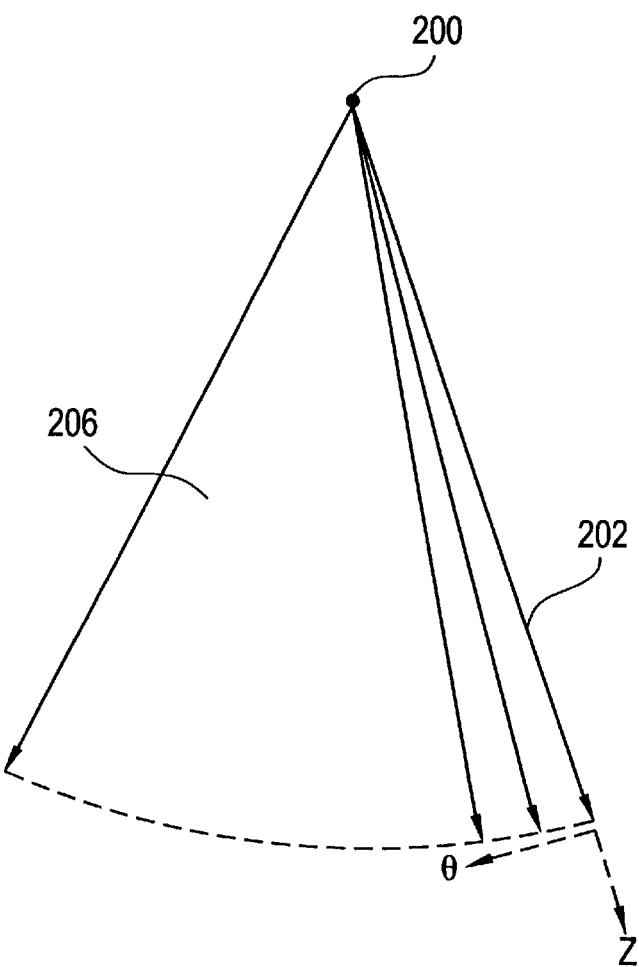
FIG. 3 pictorially shows scanning to be performed with an acoustic line moved sequentially by the system shown in FIG. 1.

An ultrasonic beam is repeatedly transmitted at predetermined intervals according to the transmission timing signal generated by the transmission timing signal generation unit 602. Accordingly, the transmission beam former 604 and reception beam former 610 change the direction of the acoustic line by a predetermined angle. Consequently, the interior of the object 4 is sequentially scanned by the acoustic line. The transmitter-receiver 6 having the foregoing components scans the object as shown in, for example, FIG. 3. Specifically, a sector-shaped two-dimensional field 206 is scanned by moving an acoustic line 202, which extends in a z direction from a radiation point 200, in a θ direction. Thus, so-called sector scan is achieved.

Figure 4:
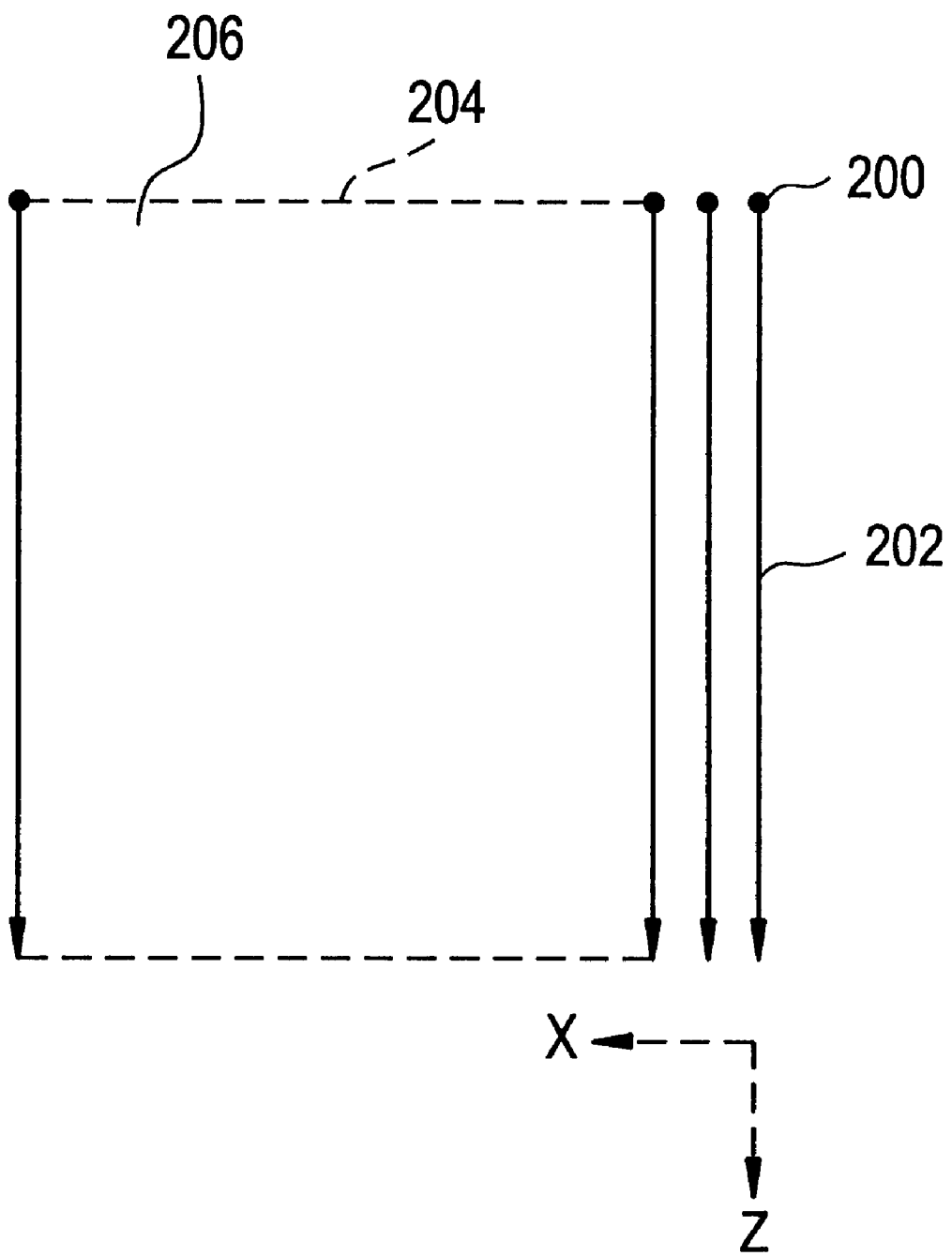
FIG. 4 pictorially shows scanning to be performed with an acoustic line moved sequentially by the system shown in FIG. 1.

When the transmission or reception aperture is formed with part of the array of ultrasonic transducers, the aperture is shifted sequentially along the array. Consequently, a scan is achieved as, for example, shown in FIG. 4. Specifically, the radiation point 200 from which the acoustic line 202 extends in the z direction is shifted in parallel along a linear trajectory 204, and a rectangular two-dimensional field 206 is scanned in an x direction to perform a so-called linear scan.

Figure 5:
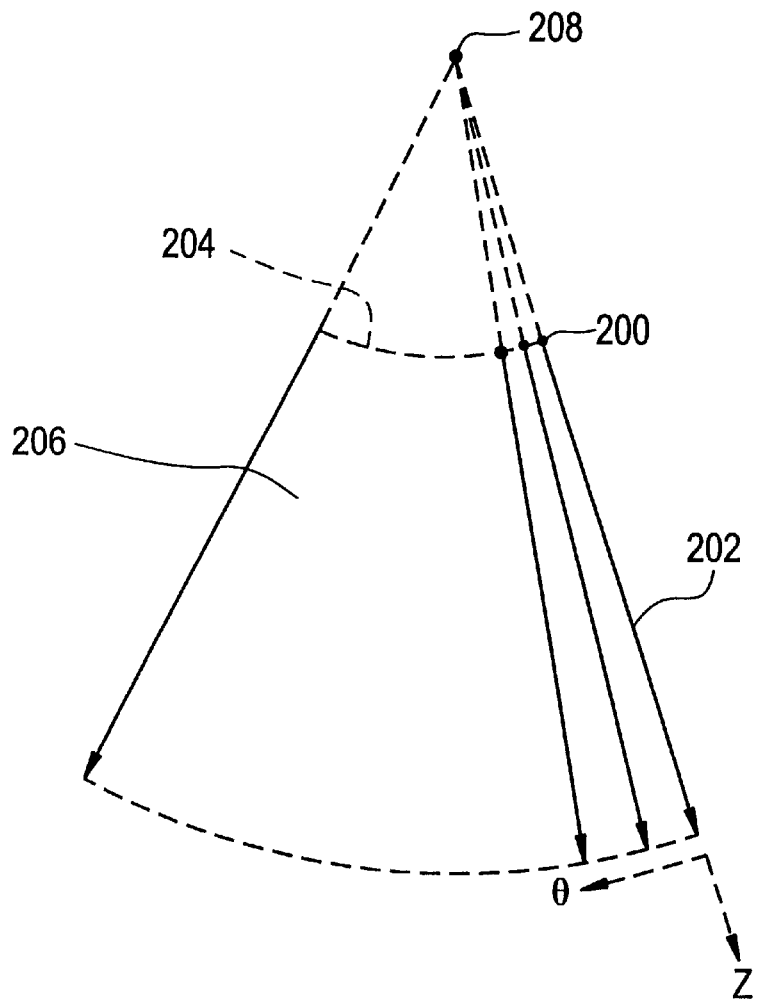
FIG. 5 pictorially shows scanning to be performed with an acoustic line moved sequentially by the system shown in FIG. 1.

When the ultrasonic transducer array is formed as a so-called convex array having ultrasonic transducers arranged like a warping arc in the direction of transmission of ultrasonic waves, the acoustic line is moved similarly to that in the linear scan. For example, as shown in FIG. 5, the radiation point 200 from which the acoustic Line 202 extends is shifted along an arc trajectory 204, and the sector two-dimensional field 206 is scanned with the acoustic line thus moved in the θ direction. Consequently, a so-called convex scan is achieved.

The transmitter-receiver 6 is connected to a B-mode processor 10 and a Doppler processor 12 respectively. An echo signal produced for each direction of the acoustic line by the transmitter-receiver 6 is transferred to the B-mode processor 10 and Doppler processor 12 respectively.

Figure 6:
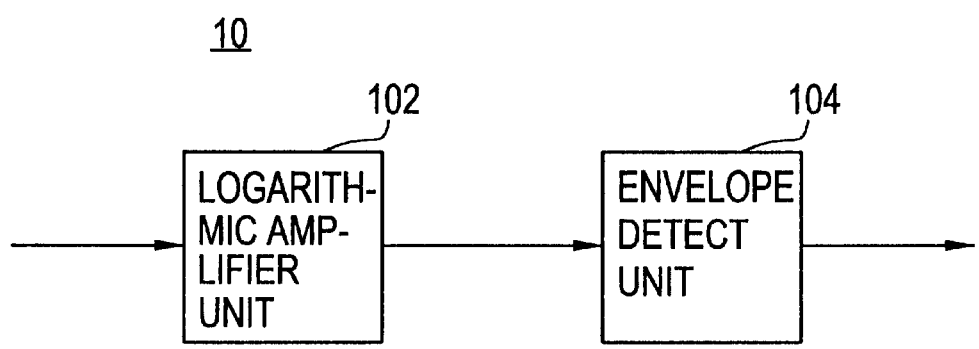
FIG. 6 is a block diagram of a B-mode processor employed in the system shown in FIG. 1.

The B-mode processor 10 produces B-mode image data. The B-mode processor 10 includes, as shown in FIG. 6, a logarithmic amplifier unit 102 and an envelope detector unit 104. In the B-mode processor 10, the logarithmic amplifier unit 102 produces a signal whose amplitude is the logarithmic function of the amplitude of the echo signal. The envelope detector unit 104 detects the envelope of the echo signal, and produces a signal that represents the intensities of echoes returned from points of reflection over the acoustic line, that is, an A-scope signal. The instantaneous amplitudes of the A-scope signal are respectively acquired as luminance values, whereby B-mode image data is produced.

The Doppler processor 12 produces Doppler image data The Doppler image data includes flow velocity data, variance data, and power data.

Figure 7:
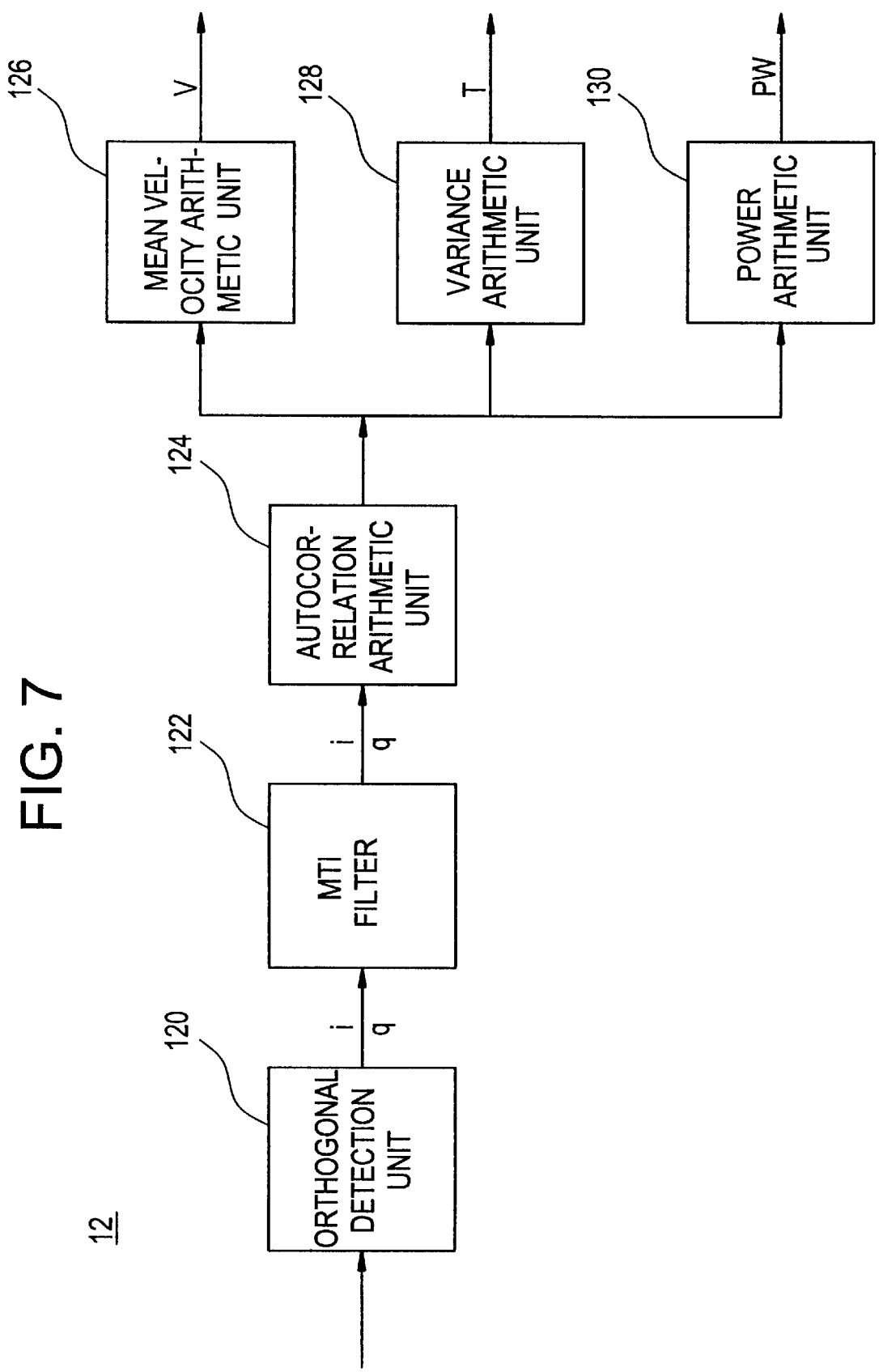
FIG. 7 is a block diagram showing part of a Doppler processor employed in the system shown in FIG. 1.

The Doppler processor 12 consists of, as shown in FIG. 7, an orthogonal detection unit 120, a moving target indication (MTI) filter 122, an autocorrelation arithmetic unit 124, a mean velocity arithmetic unit 126, a variance arithmetic unit 128, and a power arithmetic unit 130.

In the Doppler processor 12, the orthogonal detection unit 120 detects orthogonal components of the echo signal. The MTI filter 122 performs MTI processing and detects Doppler shifts represented by the echo signal. Moreover, the autocorrelation arithmetic unit 124 performs autocorrelation on the output signal of the MTI filter 122. The mean velocity arithmetic unit 126 calculates a mean flow velocity V from the result of the autocorrelation. The variance arithmetic unit 128 calculates a variance T of a flow velocity from the result of the autocorrelation. The power arithmetic unit 130 calculates the power PW of a Doppler signal from the result of the autocorrelation. Hereinafter, the mean flow velocity may be referred to simply as flow velocity. Moreover, the variance of a flow velocity may be referred to simply as variance, and the power of a Doppler signal may be referred to simply as power.

The Doppler processor 12 produces data of a flow velocity V, a variance T, and a power PW, which are concerned with an echo source that makes motion within the object 4, in relation to each direction in which the acoustic line is oriented. The data represents a flow velocity, a variance, and a power relevant to each point (depicted with a pixel) over the acoustic line. The flow velocity is calculated as a parameter dependent on each direction of the acoustic line. Moreover, the direction of a blood flow approaching the ultrasonic probe 2 and the direction of a blood flow receding from the ultrasonic probe 2 are distinguished from each other.

The B-mode processor 10 and Doppler processor 12 are connected to an image processor 14. The image processor 14 produces a B-mode image or a Doppler image according to data received from the B-mode processor 10 or Doppler processor 12.

Figure 8:
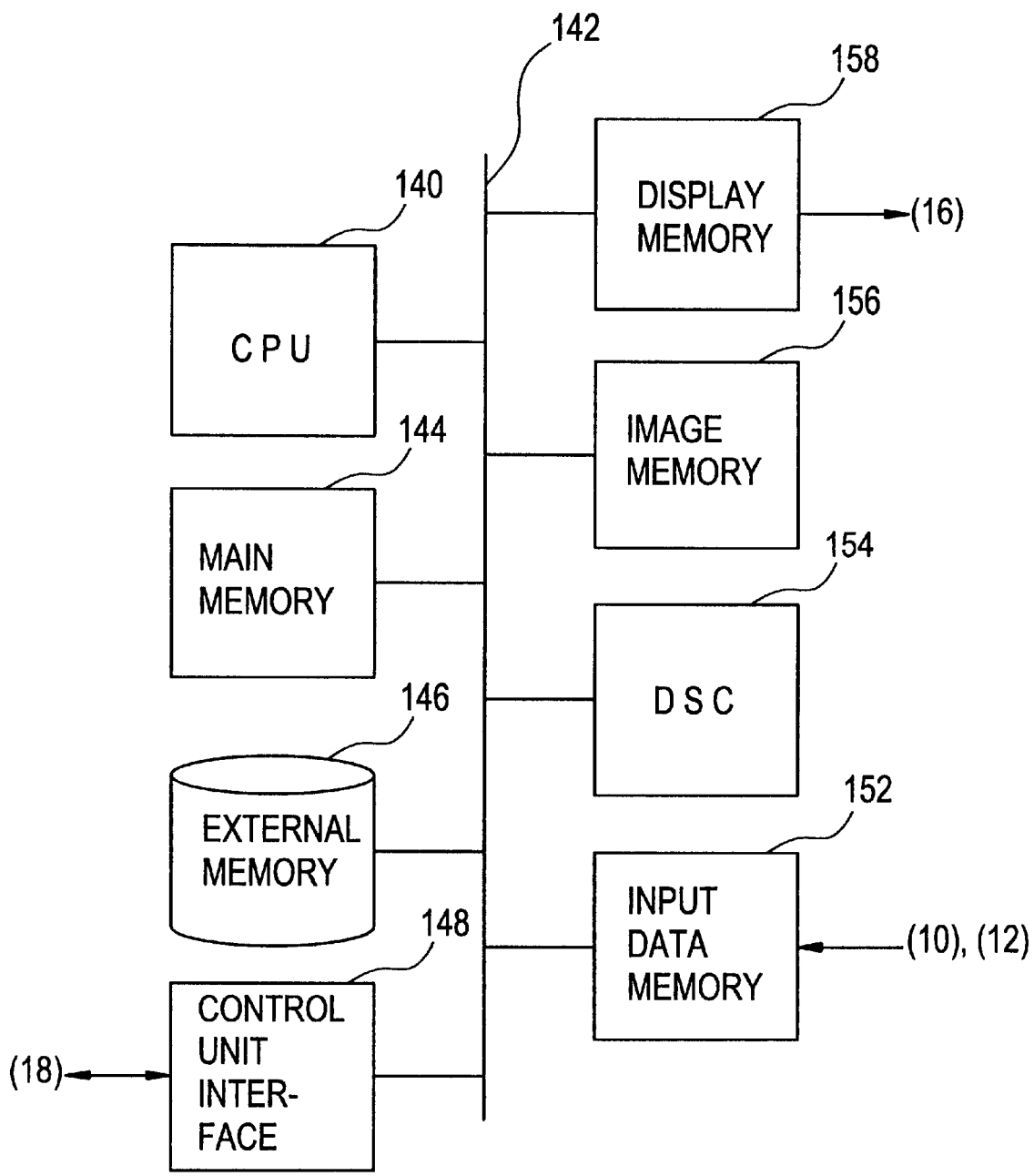
FIG. 8 is a block diagram of an image processor employed in the system shown in FIG. 1.

The image processor 14 includes, as shown in FIG. 8, a central processing unit (CPU) 140. A main memory 144, an external memory 146, a control unit interface 148, an input data memory 152, a digital scan converter (DSC) 154, an image memory 156, and a display memory 158 are connected to the CPU 140 over a bus 142.

Programs to be run by the CPU 140 are stored in the external memory 146. Moreover, various data items the CPU 140 uses to run the programs are stored in the external memory 146.

The CPU 140 loads a program from the external memory 146 to the main memory 144, and runs it to perform predetermined image processing. A program stored in the external memory 146 implements an information display feature, which will be described later, in the CPU 140. The CPU 140 transfers a control signal to or from a control unit 18, which will be described later, via the control unit interface 148 in the course of running a program.

B-mode image data and Doppler image data received from the B-mode processor 10 and Doppler processor 12 in relation to each direction of the acoustic line are stored in the input data memory 152. The data in the input data memory 152 is scanned and converted by the DSC 154, and stored in the image memory 156. The data in the image memory 156 is transferred to a display unit 16 via the display memory 158.

The display unit 16 is connected to the image processor 14. The display unit 16 receives image data from the image processor 14, and displays an image according to the image data. The display unit 16 is realized with a graphic display or the like that employs a CRT capable of displaying color images. The display unit 16 is an example of a main display means in accordance with the present invention. Hereinafter, the display unit 16 may be referred to as a monitor.

The control unit 18 is connected to the transmitter-receiver 6, B-mode processor 10, Doppler processor 12, image processor 14, and display unit 16 respectively. The control unit 18 transfers control signals to these components and controls the actions thereof. The control unit 18 receives a reporting signal from each of the controlled components. A B mode and a Doppler mode are implemented under the control of the control unit 18. The ultrasonic probe 2, transmitter-receiver 6, B-mode processor 10, Doppler processor 12, image processor 14, and control unit 18 constitute an example of an imaging means in accordance with the present invention.

An operator console 20 is connected to the control unit 18. The operator console 20 is manipulated by a user and used to enter a command or information that is transmitted to the control unit 18. The operator console 20 includes, for example, a keyboard, a pointing device, and other operating tools.

The operator console 20 includes an auxiliary display panel. The auxiliary display panel is an example of an auxiliary display means in accordance with the present invention. The auxiliary display panel will be described later.

Imaging to be performed by the imaging system will be described below. A user brings the ultrasonic probe 2 into contact with a desired place on the object 4. The operator console 20 is manipulated to initiate imaging in which, for example, both the B mode and Doppler mode are implemented. Consequently, B-mode imaging and Doppler-mode imaging are performed in a time-sharing manner under the control of the control unit 18. Specifically, every time Doppler-mode scans are performed a predetermined number of times, one B-mode scan is performed. Thus, a B-mode and Doppler-mode mixed scan is achieved.

In the B mode, the transmitter-receiver 6 scans the interior of the object 4 via the ultrasonic probe 2 by sequentially changing the direction of the acoustic line, and receives echoes sequentially. The B-mode processor 10 uses the logarithmic amplifier unit 102 to produce a signal whose amplitude is the logarithmic function of the amplitude of an echo signal received from the transmitter-receiver 6. The envelope detector unit 104 detects the envelope of the resultant signal to produce an A-scope signal. Consequently, B-mode image data is produced based on the A-scope signal in relation to each direction of the acoustic line.

The image processor 14 stores the B-mode image data, which is received from the B-mode processor 10 in relation to each direction of the acoustic line, in the input data memory 152. Consequently, an acoustic line data space is defined in the input data memory 152 and allocated to the B-mode image data.

In the Doppler mode, the transmitter-receiver 6 scans the interior of the object 4 via the ultrasonic probe 2 by sequentially changing the direction of the acoustic line, and receives echoes sequentially. At this time, transmission of ultrasonic waves and reception of echoes are performed a plurality of times relative to each direction of the acoustic line.

In the Doppler processor 12, the orthogonal detection unit 120 detects orthogonal components of the echo signal. The MTI filter 122 performs MTI processing, and the autocorrelation arithmetic unit 124 performs autocorrelation. The flow velocity arithmetic unit 126 calculates a flow velocity V, the variance arithmetic unit 128 calculates a variance T, and the power arithmetic unit 130 calculates a power PW. These calculated values are provided as data that represents a flow velocity, a variance, and a power, which are concerned with an echo source, in relation to each direction of the acoustic Line and each point over the acoustic line which is depicted as a pixel.

The image processor 14 stores Doppler image data, which is received from the Doppler processor 12 in relation to each direction of the acoustic Line and each point over the acoustic line which is depicted as a pixel, in the input data memory 152. Consequently, an acoustic line data space is defined in the input data memory 152 and allocated to each Doppler image data.

The CPU 140 instructs the DSC 154 to scan and convert the B-mode image data and Doppler image data existent in the input data memory 154. The resultant data is written in the image memory 156.

At this time, the Doppler image data is written as flow velocity distribution image data which represents the values of a flow velocity V and the values of a variance T, power Doppler image data which represents the values of a power PW and variance-inclusive power Doppler image data which represents the values of the power PW and the values of the variance T, and variance image data which represents the values of the variance T.

The CPU 140 writes B-mode image data and respective Doppler image data items in different areas. Images based on the B-mode image data and respective Doppler image data items are displayed on the display unit 16.

A B-mode image is a tomographic image of a scanned slice of an intracorporeal tissue that is scanned by moving the acoustic line. Among color Doppler images, a flow velocity distribution image is an image depicting the two-dimensional distribution of the values of the flow velocity of an echo source. In the image, a display color in which a flow is displayed is varied depending on the direction of the flow, and luminance required for the display color is varied depending on the flow velocity. Moreover, an amount of predetermined mixed color is increased according to a variance, and the purity of the display color is thus varied depending on the variance.

A power Doppler image is an image depicting the two-dimensional distribution of the values of the power of a Doppler signal. The image indicates the location of an echo source that makes motion. A luminance required for the display color of the image is proportional to the power. When the values of a variance are indicated in combination with the values of the power, an amount of predetermined mixed color is increased according to the variance and the purity of the display color is thus varied depending on the variance.

A variance image is an image depicting the two-dimensional distribution of the values of a variance, This image also indicates the location of an echo source that makes motion. Luminance required for the display color of the image is proportional to the variance.

In order to display these images on the display unit 16, the images are synthesized with a B-mode image in the display memory 158. The synthetic image is displayed on the display unit 16, whereby a color Doppler image distinctly depicting a positional relationship to an intracorporeal tissue can be viewed.

Figure 9:
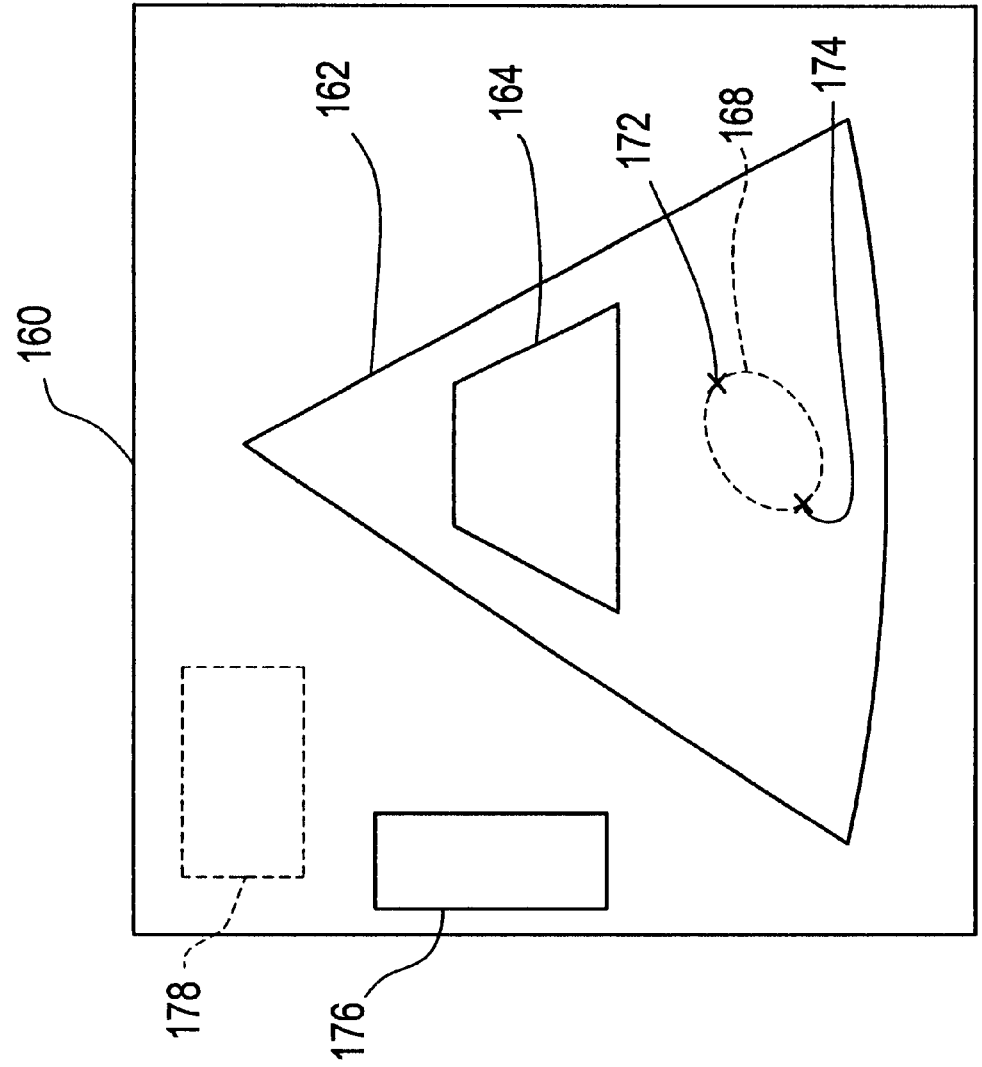
FIG. 9 schematically shows an example of an image displayed on the screen of a display unit employed in the system shown in FIG. 1.

FIG. 9 schematically shows an example of a display screen showing the above image. As illustrated, a B-mode image 162 produced through a sector scan is displayed on the screen 160. A color Doppler image 164 is displayed while being superposed on the B-mode image 162. The color Doppler image 164 is distinguished with a border between display areas allocated to the images.

A region of interest (ROI) 168 is defined in the B-mode image 162. Measurement cursors 172 and 174 are displayed at two points on the contour of the ROI 168. The measurement cursors 172 and 174 can be moved freely by a user who manipulates the pointing device.

A gray scale 176 that indicates a shade of a color in which the B-mode image 162 is displayed, and a user comment 178 are presented in an unoccupied field of the display screen 160.

Figure 10:
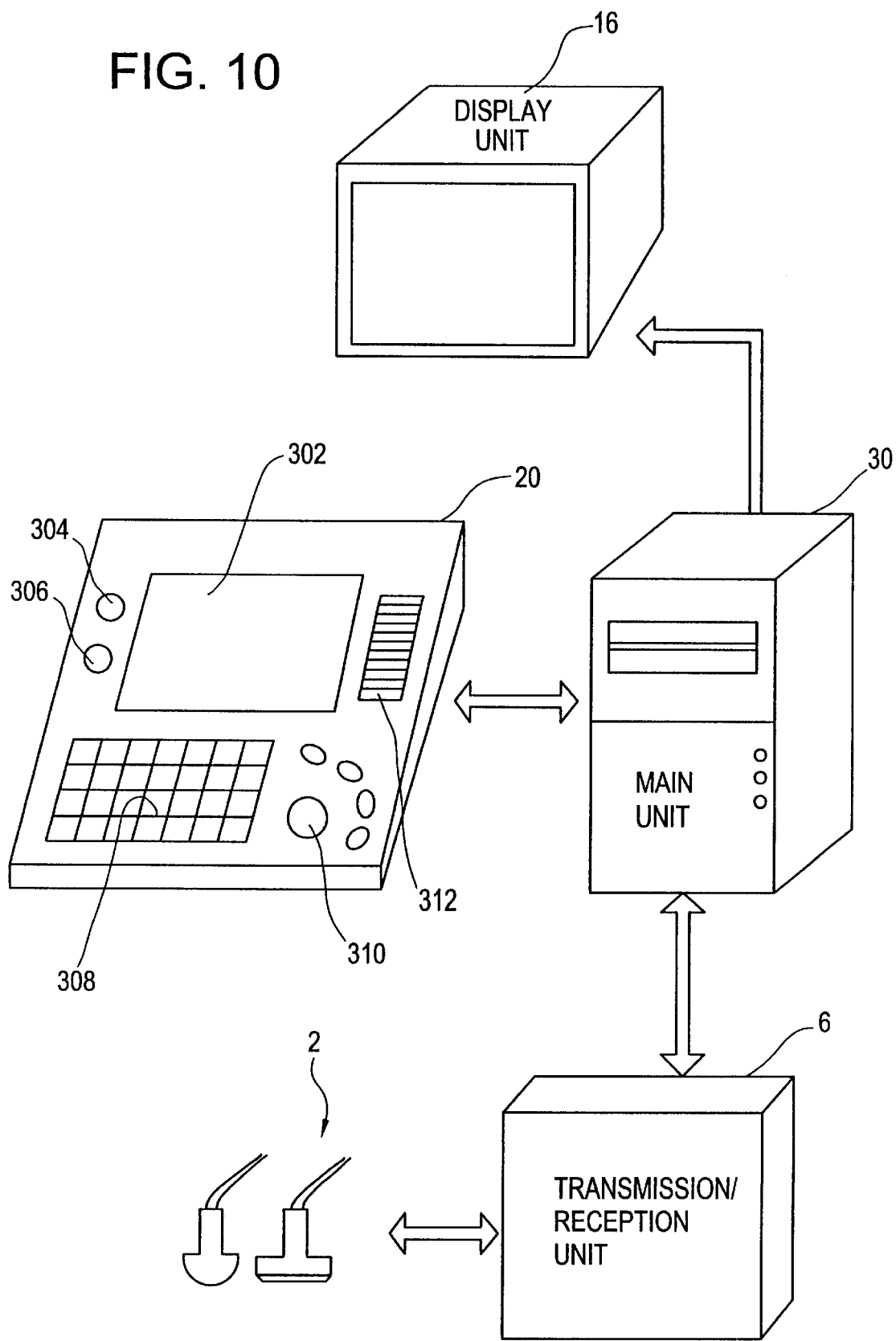
FIG. 10 schematically shows the physical configuration of the system in accordance with the embodiment of the present invention.

FIG. 10 schematically shows the physical configuration of the ultrasonic imaging system. In the drawing, the same reference numerals are assigned to the components identical to those shown in FIG. 1, and the description of the components is omitted. The B-mode processor 10, Doppler processor 12, image processor 14, and control unit 18 are incorporated in a main unit 30. The main unit 30 may be referred to as a host.

The operator console 20 includes an auxiliary display panel 302. The auxiliary display panel 302 is formed with a transmissive LCD that has a light source for illumination placed behind it. The light source for illumination may be referred to as a backlight. The auxiliary display panel 302 is an example of a display device in accordance with the present invention.

The operator console 20 has a luminance control knob 304. A user manipulates the luminance control knob 304 so as to continuously vary the luminance of the auxiliary display panel 20.

The operator console 20 also has a luminance switch 306. A user manipulates the luminance switch 306 so as to change the luminance of the auxiliary display panel 20 between two levels or among three levels. The switch is a push-button switch. With every press, when the switch permits switching of two luminance levels, the two states of the switch are switched alternately. When the switch permits switching of three luminance levels, the three states of the switch are switched cyclically. Hereinafter, the luminance switch may be referred to as a lookup table switch.

The operator console 20 also has alphanumeric keys 308, a feature switching device 310, a command enter key 312, and other appropriate operating tools.

Figure 11:
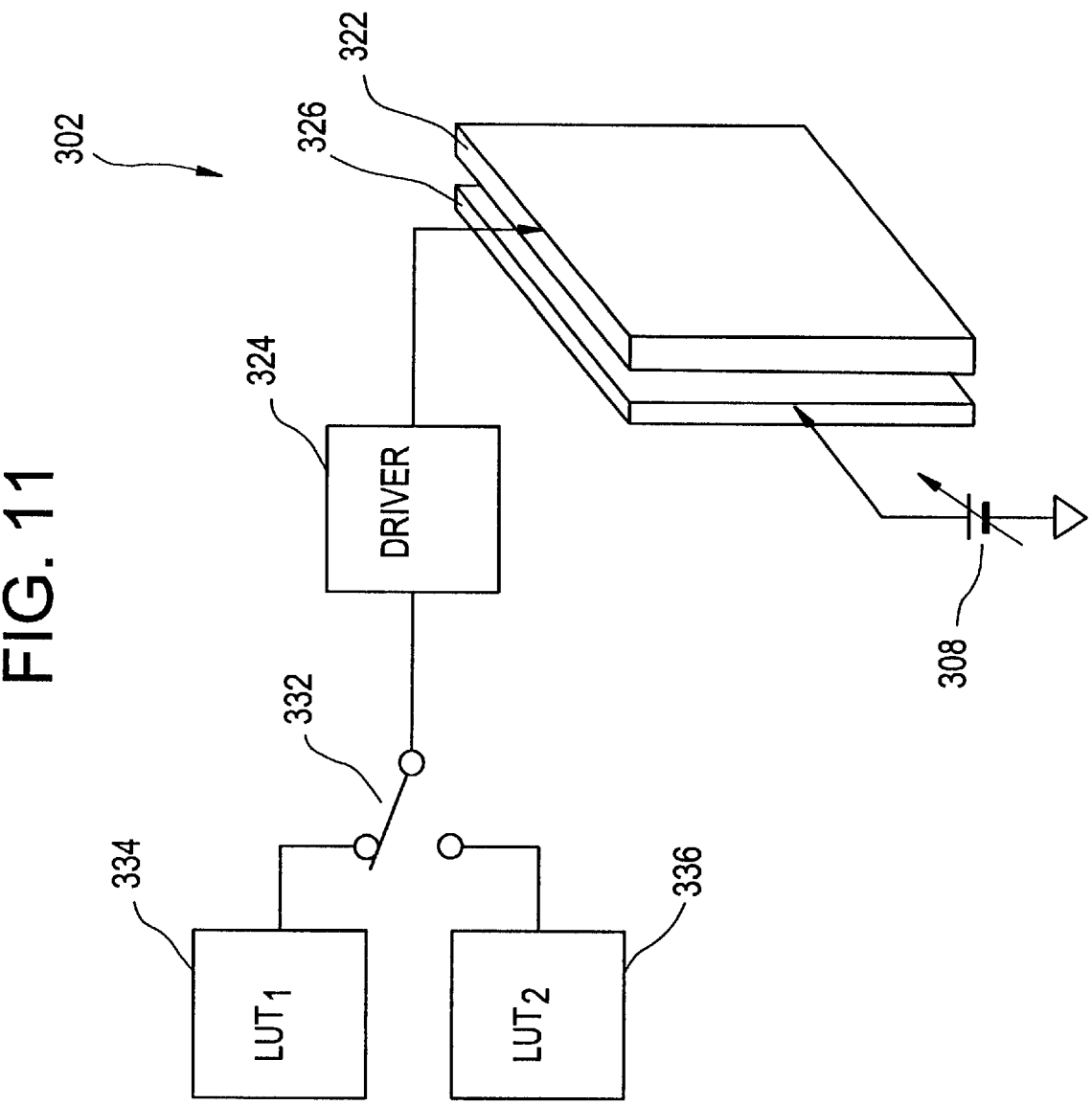
FIG. 11 is a block diagram showing components relevant to an auxiliary display panel.

FIG. 11 is a block diagram showing the components of the operator console 20 relevant to the auxiliary display panel 302. As illustrated, the auxiliary display panel 302 includes a liquid crystal panel 322, a driver 324, a backlight 326, and a backlight power supply 328. The liquid crystal panel 322, driver 324, backlight 326, and backlight power supply 328 constitute an example of an LCD in accordance with the present invention.

Either image data listed in a lookup table (LUT) 334 or image data listed in a lookup table 336 is transferred to the driver 324 via a switching device 332. The image data listed in the lookup table 334 or 336 is image data based on which a continuous-tone image is displayed on the liquid crystal panel 322. The switching device 332 has the states thereof switched with a press of the luminance switch 306.

The lookup tables 334 and 336 are created using, for example, ROMs. However, the lookup tables are not limited to ROMs. Alterative, for example, RAMs, flash memories, or any other storage media may be used to create the lookup tables.

The lookup table 334 is an example of a first memory means in accordance with the present invention. The lookup table 336 is an example of a second memory means in accordance with the present invention. The switching device 332 is an example of an image data providing means in accordance with the present invention.

The driver 324 controls the transmittance of each pixel location on the liquid crystal panel 322 according to image data. Light emanating from the backlight 326 passes through each pixel location according to the transmittance. Consequently, an image is rendered on the face of the liquid crystal panel 322.

Each pixel location includes three sub-pixel locations. Each sub-pixel location has a three-primary color filter composed of red, green, and blue filters. Diverse colors are expressed with combinations of the intensities of light passing through the three-primary color filter. The liquid crystal panel 322 is a color liquid crystal panel.

The backlight power supply 328 is a variable power supply. Power to be supplied to the backlight 326 can be continuously controlled using the luminance control knob 304. The brightness of the backlight 326 is controlled by controlling the power, to thereby control the luminance of the liquid crystal panel 322 on which an image is displayed.

Image data concerning an operating screen image is listed in the lookup table 334. A user retrieves the screen image so that the screen image will be displayed on the Liquid crystal panel 322. The screen image displayed is used to operate the imaging system. Image data is color image data representing halftones. This results in a continuous-tone color image.

Figure 12:
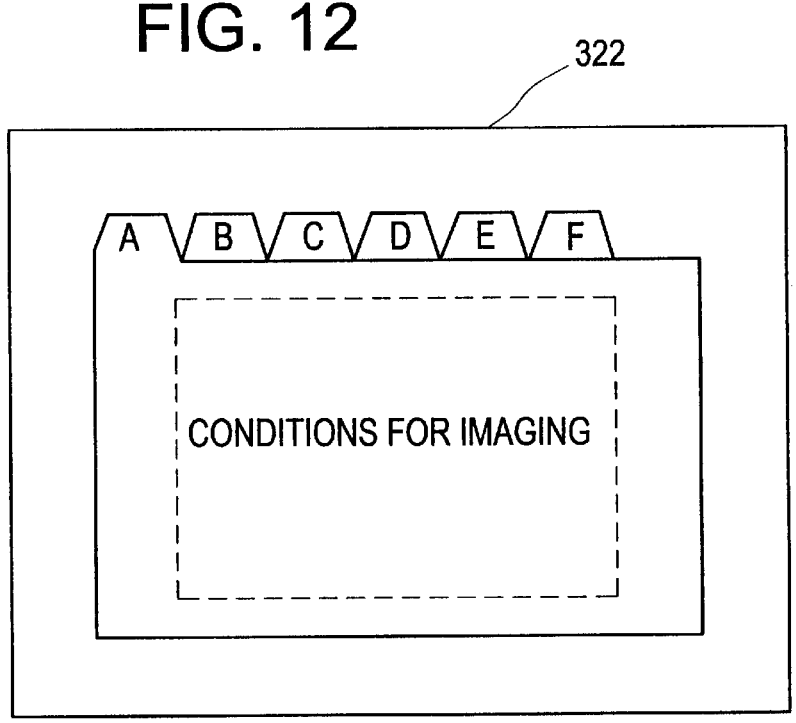
FIG. 12 schematically shows a screen displayed on the auxiliary display panel.

FIG. 12 shows an example of the operating screen image. The illustrated operating screen image presents predefined conditions for imaging for a plurality of imaging modes A to F such as the B mode, color Doppler mode, and power Doppler mode. The conditions for imaging are presented in an image that simulates a tabbed page. Referring to FIG. 12, the conditions for imaging for the imaging mode A are presented in the uppermost one of overlapping pages.

If a desired tab is designated using the command enter key 312, the page bearing the tab can be opened. A user checks the conditions for imaging before starting imaging.

Image data representing the same screen image is listed in the lookup table 336. However, although the image data represents an image whose composition is the same as the composition of the image represented by the image data listed in the lookup table 334, the image is darker.

Based on the image data, the transmittance at each pixel location on the liquid crystal panel 322 is made lower than the transmittance specified in the image data listed in the lookup table 334. The image data specifying the lower transmittance can be said to be image data that specifies lower lightness, which is one of three factors determining a display color along with saturation and hue.

Figure 13:
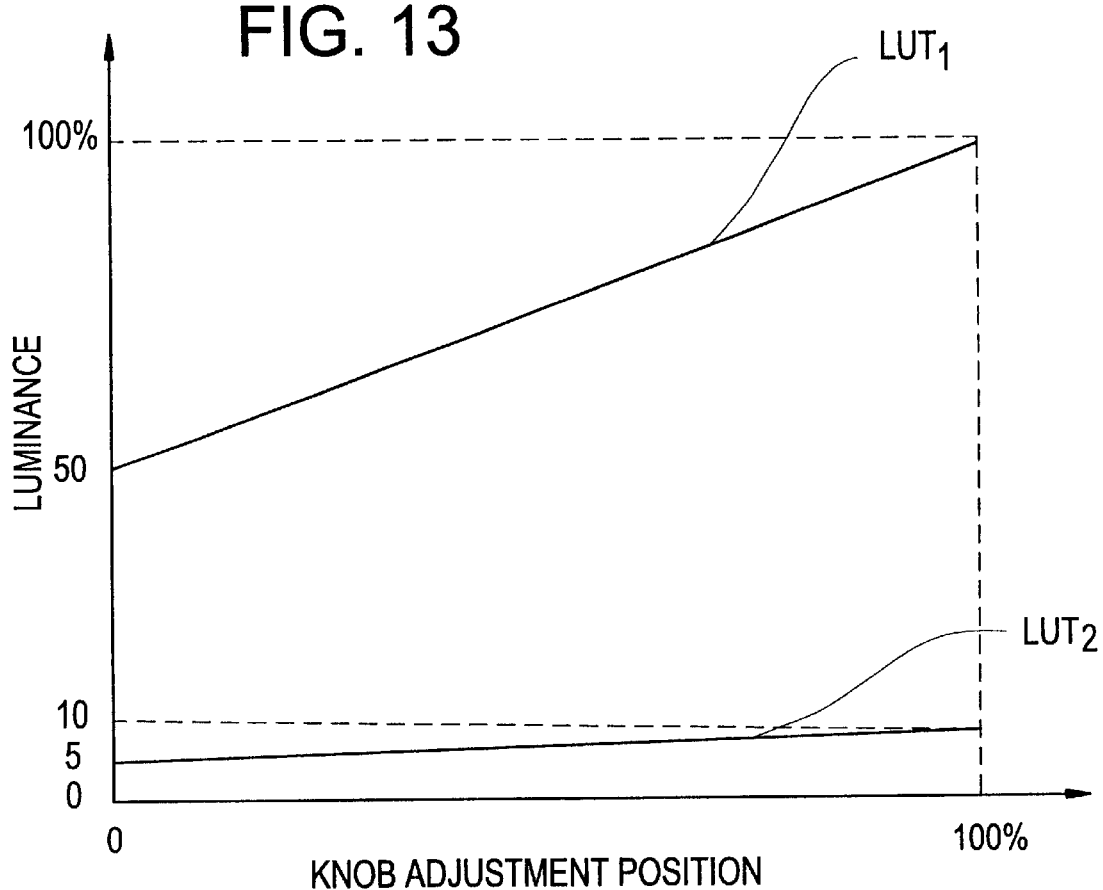
FIG. 13 is a graph indicating the range of the values of the luminance exhibited by a screen of the auxiliary display panel.

The lower transmittance is, for example, a one-tenth of the transmittance specified in the image data listed in the lookup table 334. Consequently, assuming that the luminance of the screen based on the image data listed in the lookup table 334 varies within the range from 50% to 100% in response, for example, to the range from 0% to 100% of the luminance control knob 304 shown in FIG. 13, the luminance thereof based on the image data listed in the lookup table 336 varies within the range from 5% to 10%. The two luminance variation curves are concerned with the brightest images represented by image data listed in the lookup tables.

Conventionally, the luminance can only be lowered to 50% according to conventional luminance control, that is, a luminance control method of adjuring the luminance control knob 304 alone. In the present imaging system, the luminance can be lowered to 5%.

The transmittance of the liquid crystal panel is varied depending on not only a lightness but also a hue. In other words, an image containing light colors appears bright because it requires a high transmittance, while an image containing dark colors appears dark because it requires a low transmittance. Image data representing images that contain light colors is listed in the lookup table 334, while image data representing images that contain dark colors is listed in the lookup table 336. The luminance of the display screen can be changed by switching the lookup tables.

Figure 14A:
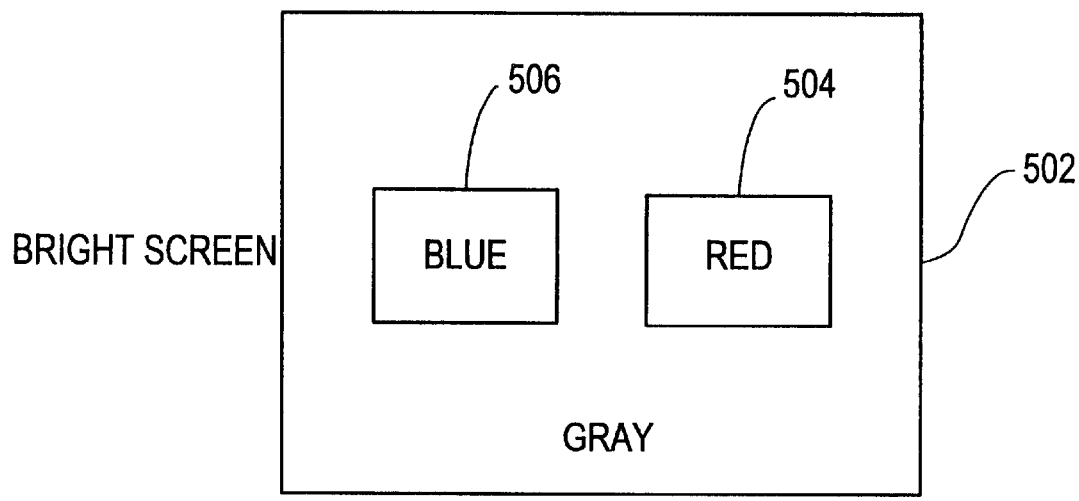
FIG. 14 schematically shows screens displayed on the auxiliary display panel.
Figure 14B:
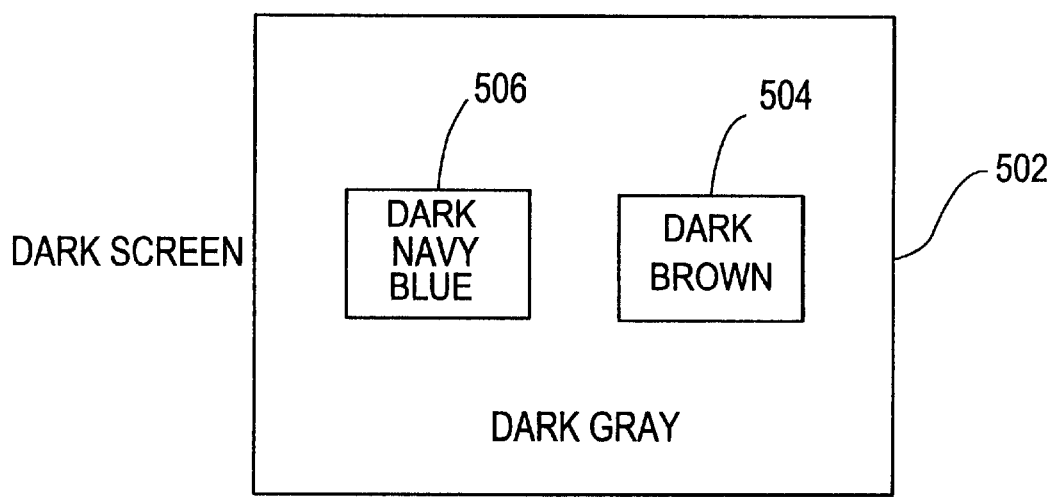

FIG. 14 pictorially shows examples of bright and dark screens. FIG. 14(1) shows the example of a bright screen image. A screen 502 contains an operating button 504 expressed in red against a gray background, and an operating button 506 expressed in blue. The operating buttons 504 and 506 serve as graphical user interfaces (GUIs). FIG. 14(2) shows the example of a dark screen image. A screen 502 contains an operating button 504 expressed in dark brown against a dark gray background, and an operating button 506 expressed in dark blue.

The transmittance of the liquid crystal panel is varied depending on both lightness and hue. Specifically, image data representing images that contain light colors and exhibit high lightness is listed in the lookup table 334, while image data representing images that contain dark colors and exhibit low lightness is listed in the lookup table 336. The brightness of a displayed image can be varied by switching the lookup tables. In this case, the difference in brightness between the bright screen image and dark screen image shown in FIG. 14 can be further intensified FIG. 15 is a flowchart describing actions to be performed in the present imaging system according to manipulations performed on the operator console 20. As described in the drawing, at step 402, a user turns on the power supply of the present imaging system, that is, the imaging system has the power supply turned on.

As soon as the power supply is turned on, an operating screen based on image data listed in the lookup table 334 is displayed on the auxiliary display panel 302 of the operator console 20 at step 404.

At step 406, the user corrects the luminance using the luminance control knob. In other words, the luminance control knob is used to control the backlight 326 and to thus control the luminance of the screen.

Thereafter, at step 408, the user selects the conditions for imaging (menu).

Accordingly, at step 410, the host brings the system to a state dependent on the conditions for imaging, and starts displaying an image on the monitor.

At step 412, the user checks if the screen of the LCD, that is, the auxiliary display panel 302 is dazzling.

If the display screen is not dazzling, a patient is scanned, that is, an object is imaged at step 414.

After one scan is completed, control is returned to step 406. The same actions as those described above are performed for the next scan. Unless the display screen is not found dazzling, the above actions are repeated.

If the display screen is found dazzling, the lookup table switch 306 is pressed at step 416.

Consequently, an image based on image data listed in the lookup table 336 is displayed on the auxiliary display panel 302 at step 418. Thus, the image gets darker, and the screen is no longer dazzling.

At step 420, a patient is scanned.

After one scan is completed, the lookup table switch 306 is pressed at step 422.

Consequently, the bright image based on the image data listed in the lookup table 334 is displayed on the auxiliary display panel 302 at step 424.

Thereafter, control is returned to step 406, and the subsequent steps are followed. If the screen of the auxiliary display panel 302 is dazzing, the foregoing actions are repeated.

Figure 16:
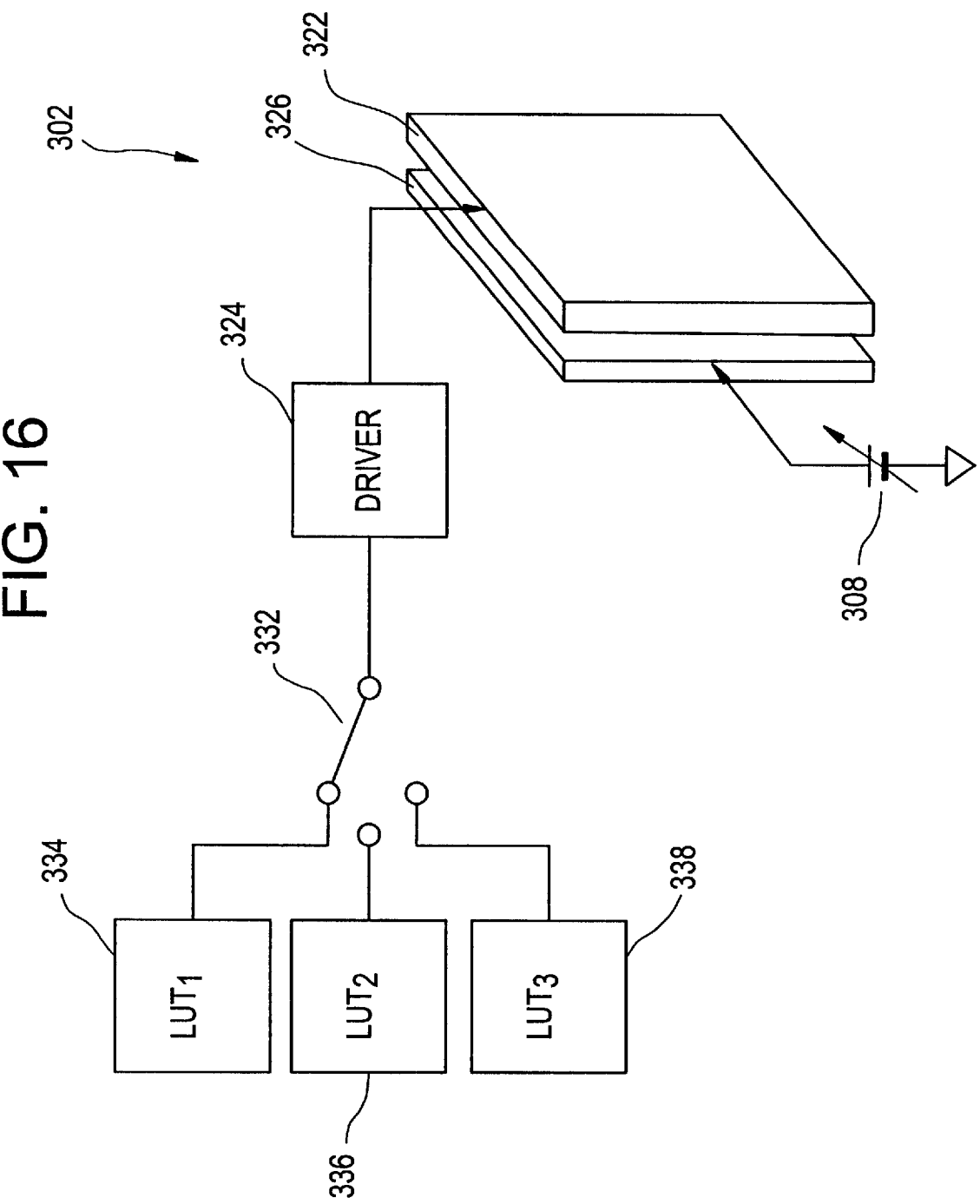
FIG. 16 is a block diagram showing components relevant to the auxiliary display panel.

FIG. 16 is a block di showing other components relevant to the auxiliary display panel 302. In the drawing, the same reference numerals are assigned to components identical to those shown in FIG. 11, and the description of the components is omitted.

The components shown in FIG. 16 include, in addition to the same components as those shown in FIG. 11, a lookup table 338. Any of the lookup tables 334, 336, and 338 which is selected with the switching device 332 is connected to the driver 324.

The lookup tables 334, 336, and 338 are created using, for example, ROMs. However, they are not limited to ROMs. Alternatively, RAMS, flash memories, or any other storage media may be used to create them.

The lookup table 334 is an example of a first memory means in accordance with the present invention. The lookup table 336 is an example of a second memory means in accordance with the present invention. The lookup table 338 is an example of a third memory means in accordance with the present invention. The switching device 332 is an example of an image data providing means in accordance with the present invention.

The aforesaid image data is listed in the lookup tables 334 and 336. Image data representing a darker image than the image represented by the image data listed in the lookup table 336 is stored in the lookup table 338.

The image data represents an achromatic image, that is, a gray or black image devoid of colors having the same composition as the images represented by the image data listed in the lookup tables 334 and 336.

Figure 17A:
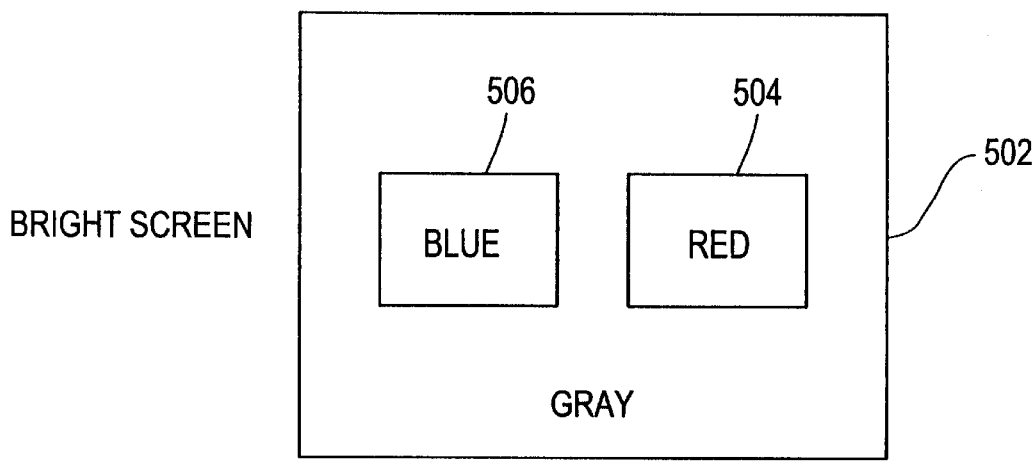
FIG. 17 schematically shows screens displayed on the auxiliary display panel.
Figure 17B:
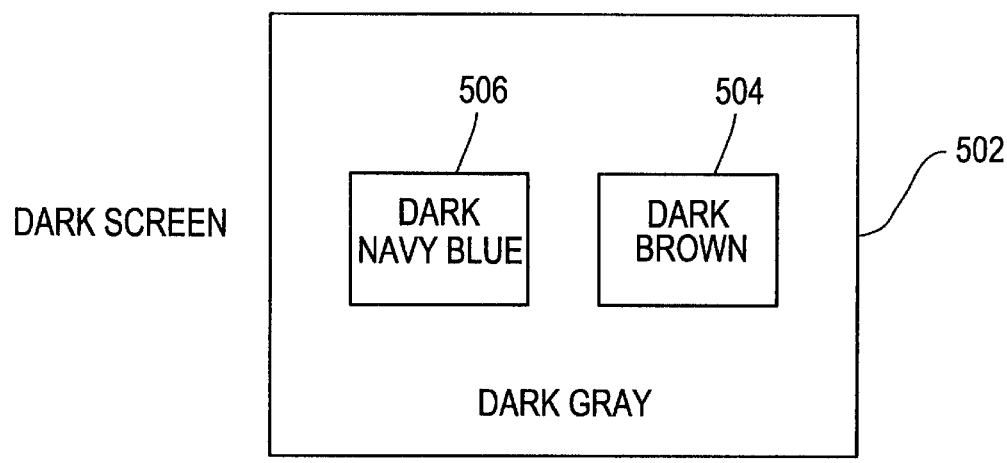
Figure 17C:
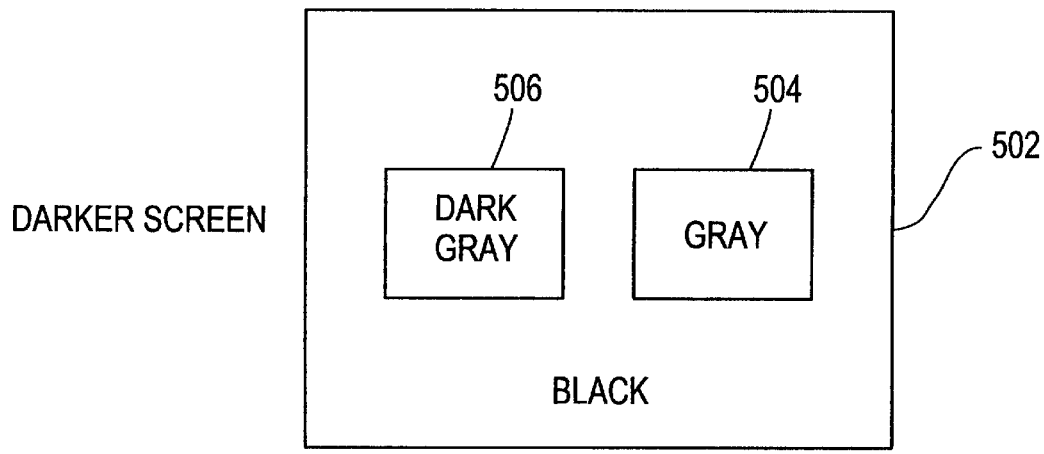

Consequently, a darker screen that contains, for example, as shown in FIG. 17(3), an operating button 504 expressed in gray against a black background and an operating button 506 expressed in dark gray is displayed.

FIG. 18 is a flowchart describing actions to be performed in the present imaging system that includes the auxiliary display panel 302. In the drawing, the same reference numerals are assigned to steps identical to those described in FIG. 15, and the description of the steps is omitted.

At step 418, an image based on image data listed in the lookup table 336 is displayed to judge, at step 426, whether the LCD is hazzling.

If the LCD is no longer dazzling, a patient is scanned at step 420 as mentioned above.

If the LCD is found dazzling, the lookup table switch 306 is pressed at step 428.

Consequently, a screen based on image data listed in the lookup table 338 is displayed on the auxiliary display panel 302. Thus, the screen gets darker and the display screen is no longer dazzling.

At step 420, a patient is scanned.

After one scan is completed, the lookup table switch 306 is pressed at step 422.

Consequently, at step 424, a bright screen based on image data listed in the lookup table 334 is displayed on the auxiliary display panel 302.

Control is then returned to step 406, and the subsequent steps are followed. If the screen of the auxiliary display panel 302 is dazzling, the above actions are repeated.

The present invention has been described based on the preferred embodiment. People with ordinary skill in the field of industries to which the present invention belongs would be able to change or replace various parts of the aforesaid embodiment without a departure from the technological scope of the invention. The technological scope of the invention includes not only the aforesaid embodiment but also all working modes set forth in claims.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic imaging system comprising:

imaging means for transmitting ultrasonic waves and for producing images of a subject according to received echos of said ultrasonic waves;

main display means for displaying said images of said subject; and auxilliary display means for displaying, concurrently with dispay of said images of said subject, images of information for operating said system; wherein said auxilliary display means comprises:

an LCD for radiating lights of differing brightnesses and hues which are emitted from behind forwards through a liquid crystal matrix controllable to provide different brightnesses and hues at each pixel location thereby to display said images of said information at a selected brightness or hue;

first memory means for storing first data based on which a predetermined image of said information of a particular brightness or hue is displayed on said LCD;

second memory means for storing second data based on which the same predetermined image of said information is displayed on said LCD but with a brightness or hue which is different from said particular brightness or hue; and selecting means for providing to said LCD either said first data so as to cause said LCD to display said predetermined image of said information of a particular brightness or hue or said second data so as to cause said LCD to display said predetermined image of said information of said different brightness or hue;

whereby said auxilliary display means displays said predetermined image of said information of desired brightness or hue concurrently with display of said image of said subject on said main display means.

2. The system of claim 1, wherein said selecting means is manipulated manually.

3. The system of claim 1, wherein amount of light to be emitted to said LCD from behind is variable.

4. The system of claim 1, wherein said LCD displays color.

5. The system of claim 1, wherein said liquid crystal matrix has a transmittance which is controlled at each pixel, and said predetermined image of said information is displayed on said LCD with a lower luminescence than said particular brightness.

6. The system of claim 1, wherein said liquid crystal matrix controls hue of each pixel, and said predetermined image of said information is displayed on said LCD with a darker hue than said particular hue.

7. The system of claim 1, further comprising third memory means for storing third data based on which said predetermined image of said information is displayed on said LCD in a darker achromatic color than said different brightness or hue.

8. The system of claim 1, wherein said liquid crystal matrix controls brightness and hue of each pixel, and said different hue is lower and darker than said particular hue.

9. The system of claim 1, further comprising third memory means for storing third data based on which said predetermined image of said information is displayed on said LCD in a darker achromatic color than said different brightness or hue.

* * * * *